United States Patent
Urakawa et al.

(10) Patent No.: US 7,335,811 B2
(45) Date of Patent: Feb. 26, 2008

(54) METHOD FOR COLLECTING CELLS IN M PHASE OR $G_1$ PHASE AND METHOD FOR NUCLEAR TRANSPLANTATION USING THE CELLS

(75) Inventors: Manami Urakawa, Hokkaido (JP); Yoshito Aoyagi, Hokkaido (JP)

(73) Assignee: The Japanese Research Association for Animal Embryo Transfer Technology c/o Livestock Improvement Association of Japan, Tokyo (JP)

( * ) Notice: Subject to any disclaimer, the term of this patent is extended or adjusted under 35 U.S.C. 154(b) by 375 days.

(21) Appl. No.: 10/196,203

(22) Filed: Jul. 17, 2002

(65) Prior Publication Data
US 2003/0044974 A1    Mar. 6, 2003

(30) Foreign Application Priority Data
Aug. 14, 2001 (JP) ............................. 2001-245948

(51) Int. Cl.
*A01K 67/00* (2006.01)
*A01K 67/027* (2006.01)
*C12N 15/00* (2006.01)
*C12N 5/00* (2006.01)

(52) U.S. Cl. .............................. 800/24; 800/8; 800/14; 800/21; 435/325; 435/374; 435/375; 435/376; 435/378; 435/379

(58) Field of Classification Search ................. 435/4, 435/325, 375, 455; 800/8, 21, 24, 25
See application file for complete search history.

(56) References Cited

U.S. PATENT DOCUMENTS
2001/0053550 A1* 12/2001 Stice ...................... 435/455

FOREIGN PATENT DOCUMENTS

| JP | 2001-186827 A | 7/2001 |
|---|---|---|
| WO | WO 99/37143 A2 | 7/1999 |
| WO | WO 00/42174 A1 | 7/2000 |
| WO | WO 00/51424 A2 | 9/2000 |
| WO | WO 01/45500 A1 | 6/2001 |
| WO | WO-01/49106 A2 | 7/2001 |
| WO | WO 01/68831 A2 | 9/2001 |

OTHER PUBLICATIONS

Kasinathan et al (Biol Reprod. 64(5):1487-93. 2001.*
Boquest et al, Biol. Reprod. 60:1013-1019, 1999.*
Ideta et al, Early morphological nuclear events and developmental capacity of embryos reconstructed with fetal fibroblasts at the M or G1 phase after intracytoplasmic nuclear injection in cattle. J Reprod Dev. 51(2):187-94,2005.*
Urakawa et al, Examination of a modified cell cycle synchronization method and bovine nuclear transfer using synchronized early G1 phase fibroblast cells. Theriogenology. 62(3-4):714-28, 2004.*
Hesham Attala et al., *Biochemical and Biophysical Research Communications*, vol. 228, (1996), pp. 467-473.
T. Terasima et al., *Experimental Cell Research*, vol. 30, (1963), pp. 344-362.
Jose Manuel Andreu et al., *Proc. Natl. Acad. Sci.*, vol. 79, (Nov. 1982), pp. 6753-6756.
Kevin W. Farrell et al., *Biochemistry*, vol. 19, (1980), pp. 3048-3054.
Elton Stubblefield et al., *J. Cell Physiol.*, vol. 69, (1967), pp. 345-354.
James C. Lee et al., *Biochemistry*, vol. 19, (1980), pp. 6209-6215.
Gary W. Zieve et al., *Experimental Cell Research*, vol. 126, (1980), pp. 397-405.
I. Wilmut et al., *Nature*, vol. 385, (Feb. 27, 1997), pp. 810-813.
W.A. Kues et al., *Theriogenology*, vol. 53, Abstr. 228, (2000).
T.T. Peura, *Theriogenology*, vol. 55, Abstr. 285, (2001).
J.L. Edwards et al., *Theriogenology*, vol. 55, Abstr. 265, (2001).
Hesham Attalla et al., *Cancer Genet. Cytogenet.*, vol. 102, (1998), pp. 139-141.
Y. Aoyagi et al., *Theriogenology*, vol. 41, Abstr. 157, (1994).
S.M. Willadsen, *Nature*, vol. 320, (1986), pp. 63-65.
Yoshito Aoyagi et al., *J. Reprod. Dev.*, vol. 40, (1994), pp. j5-j11.
Wakayama, Teruhiko et al., PNAS, vol. 96, No. 26, pp. 14984-14989 (Dec. 21, 1999).
Wakayam, Teruhiko et al., PNAS, vol. 96, No. 26, pp. 14984-14989 (Dec. 21, 1999).

* cited by examiner

*Primary Examiner*—Sumesh Kaushal
(74) *Attorney, Agent, or Firm*—Birch, Stewart, Kolasch & Birch, LLP

(57) ABSTRACT

Methods for collecting cells in M phase or $G_1$ phase, by which the percentage of M phase or $G_1$ phase cells is higher than that attained by the conventional methods are disclosed.

4 Claims, No Drawings

METHOD FOR COLLECTING CELLS IN M PHASE OR $G_1$ PHASE AND METHOD FOR NUCLEAR TRANSPLANTATION USING THE CELLS

This application claims priority to a foreign application JP2001-245948, filed Aug. 14, 2001.

BACKGROUND OF THE INVENTION

I. Field of the Invention

The present invention relates to a method for collecting cells in M phase (mitotic phase) or $G_1$ phase and method for nuclear transplantation using the cells.

II. Description of the Related Art

It is important to obtain a population of cells in the same particular cell cycle for clarifying the biochemical reactions which occur in the particular cell cycle, the mechanism of cell proliferation and the like. Among the methods for synchronizing the cell cycle to metaphase of cell division, the shaking method by Terashima et al[1] utilizes the fact that the cells in the metaphase of cell division are spherical and their adhesiveness with the culture plate is small, so that they are easily peeled off therefrom, which enables collection of the cells synchronized to metaphase of cell division without changing the physiological state. In their method, a portion of the culture medium is lightly blown to the surface of the culture medium with a pipette, and the cells detached thereby are collected. Among the thus collected cells, 76.6 to 87.4% thereof are in the M phase of cell cycle, but a population of cells which are entirely in the metaphase cannot be collected by their method.

On the other hand, for synchronizing the cell cycle to metaphase, colchicin[2,3], colcemid[4], nocodazole[5] or the like is usually employed. Zieve et al[6] treated the cells with nocodazole and collected cells by the shaking method to obtain cells in the metaphase in an amount of 25 to 34%. However, the efficiency of collecting the cells in metaphase is thus low.

By the recent nuclear transplantation technology using somatic cells, a viable offspring was successfully produced using the nuclei of the cells induced to $G_0/G_1$ phase by serum starvation. This technology is also useful for investigating behavior of the nuclei of the embryos whose nuclei were transplanted from cells in a particular cell cycle, and for clarifying the mechanism of development. That is, in 1997, Wilmut et al succeeded in producing a viable offspring by nuclear transplantation using somatic cells[7]. In their method, the cell cycles of the cells to be used as nuclear donors are synchronized to $G_0/G_1$ phase by culturing sheep mammary gland cells, and by decreasing the serum concentration in the culture medium from 5% to 0.05% after growing the cells, thereby subjecting the cells to serum starvation. This method is now widely used in preparation of nuclear donors. However, this method has a drawback in that fragmentation of DNAs in the cells subjected to the serum deprivation more frequently occurs than the cells not subjected to the serum deprivation[8,9], so that the percentage of the surrogate mothers who cannot continue pregnancy is high[10] when the cells subjected to serum deprivation are used as the nuclear donors. As a result, the efficiency of producing somatic clone is low, which is problematic.

SUMMARY OF THE INVENTION

Accordingly, an object of the present invention is to provide a method for collecting cells in M phase or $G_1$ phase by which the ratio of the cells in the desired phase is higher than that attained by the conventional methods. Another object of the present invention is to provide a method for nuclear transplantation by which the percentage of the reconstructed embryos that grow at least to compacted morula is higher than that attained by the conventional methods.

The present inventors intensively studied to discover that the percentage of the cells in M phase in the collected population of cells may be largely increased by (1) culturing mammalian cells on a support in the presence of an agent for synchronizing cell cycle to metaphase; (2) shaking the support and recovering cells detached from the support; and (3) recovering cells having a diameter of not less than 20 µm from the cells recovered in the step (2). The present inventors also discovered that the percentage of the cells in $G_1$ phase in the collected population of cells may be largely increased by (1) culturing mammalian cells on a support in the presence of an agent for synchronizing cell cycle to metaphase; (2) shaking the support and recovering cells detached from the support; (3) culturing cells recovered in the step (2) in the absence of an agent for synchronizing cell cycle to metaphase; and (4) recovering cells having a diameter of not more than 15 µm from the cells cultured in the step (3). Further, the present inventors intensively studied to discover that the percentage of the reconstructed embryos which grow at least to compacted morula is significantly increased by using $G_1$ phase cells as nuclear donors in nuclear transplantation to enucleated oocytes.

That is, the present invention provides a method for collecting cells in M phase comprising, in the order mentioned, the steps of:

(1) culturing mammalian cells on a support in the presence of an agent for synchronizing cell cycle to metaphase;
(2) shaking said support and recovering cells detached from said support; and
(3) recovering cells having a diameter of not less than 20 µm from the cells recovered in said step (2).

The present invention also provides a method for collecting cells in $G_1$ phase comprising, in the order mentioned, the steps of:

(1) culturing mammalian cells on a support in the presence of an agent for synchronizing cell cycle to metaphase;
(2) shaking said support and recovering cells detached from said support;
(3) culturing cells recovered in said step (2) in the absence of an agent for synchronizing cell cycle to metaphase; and
(4) recovering cells having a diameter of not more than 15 µm from the cells cultured in said step (3).

The present invention further provides a method for collecting cells in $G_1$ phase comprising culturing said cells in M phase collected by said method according to the present invention so as to allow each of the cells to divide into two cells; and recovering uniformly divided cells separately.

The present invention still further provides a method for nuclear transplantation comprising transplanting said cell collected by said method according to the present invention, or at least the nucleus thereof, to an enucleated oocyte; and culturing the resulting cell to allow it to divide.

The present invention still further provides a method for producing a somatic cell clonal mammal, comprising obtaining divided cells by the method according to the present invention, and making a mammal conceive said divided cells to become impregnated, said mammal to be impregnated belonging to the same species as the mammal from which the embryo was originated.

By the present invention, methods for collecting cells in M phase or $G_1$ phase, by which the percentage of M phase or $G_1$ phase cells is higher than that attained by the conventional methods, were provided. Further, by the present invention, a method for nuclear transplantation by which the percentage of the reconstructed embryos that grow at least to compacted morula is significantly increased, by which the cells are not subjected to serum deprivation, was provided. Since a population of cells whose cell cycles are substantially synchronized to M phase or $G_1$ phase can be obtained by the method of the present invention, the present invention is very useful for the studies of biochemical reactions occurring during the particular cell cycle, and for the studies of the mechanism of cell growth. In the method of the present invention, it is not necessary to subject the cells to serum deprivation, so that there is no possibility that the cells are adversely affected by the serum deprivation. Further, since the probability that the reconstructed embryos that grow at least to compacted morula is significantly increased by the method of the present invention, the method of the present invention is expected to largely contribute to the production of somatic clones.

DETAILED DESCRIPTION OF THE PREFERRED EMBODIMENTS

The method for collecting M phase cells will now be firstly described.

The cells subjected to the method of the present invention are mammalian cells. The species of the mammals are not restricted. Examples of the mammals include large cattle such as bovine, swine, sheep, goat and horse; rodents such as mouse and rat; and primates such as monkey, but the mammals are not limited to those mentioned above. The tissues and organs from which the cells are originated are also not restricted at all. Any cells originated from any tissue or organ may be employed, and the cells may be either somatic cells or germ cells. However, the cells which cannot be cultured in the state of being attached to a support, such as blood cells, are not compatible to this method. Cells to which foreign genes have been introduced, or cells in which a particular gene is knocked out may also be employed. In cases where production of a clone animal to which a foreign gene is introduced is aimed at, fibroblast cells may preferably be employed in view of ease of introduction of the foreign gene.

In the step (1) of the method for collecting cells in M phase according to the present invention, mammalian cells are cultured on a support in the presence of an agent for synchronizing cell cycle to metaphase. The term "cultured on a support" herein means that the cells are cultured in the state of being attached to the support. Except for a type of cells such as blood cells, which do not have the property to grow in the state of being attached to a support, mammalian cells naturally grow in the state of being attached to a support when cultured by an ordinary method on the support. As the support, petri dishes made of plastics or glass may be used, but the support is not restricted thereto.

The culture medium used for the culture in the step (1) contains an agent for synchronizing cell cycle to metaphase (the agent is hereinafter referred to as "metaphase-synchronizing agent" for short). The metaphase-synchronizing agent is not restricted and any known metaphase-synchronizing agent may be employed. Preferred examples of the metaphase-synchronizing agent include 2-methoxyestradiol[11),12)], colchicine[2),3)], colcemid[4)] and nocodazole[5)]. Among these, 2-methoxyestradiol is especially preferred, but the metaphase-synchronizing agent is not restricted to those mentioned above. The concentration of the metaphase-synchronizing agent is not restricted and may be appropriately selected depending on the type of the metaphase-synchronizing agent. For example, in case of 2-methoxyestradiol, the concentration may be about 0.5 µM to 1.5 µM, preferably about 0.8 µM to 1.2 µM. The suitable concentration of a metaphase-synchronizing agent may easily be determined by a routine experiment using a plurality of concentrations of the metaphase-synchronizing agent (see Comparative Example 2).

The culture medium used in the step (1) may be a culture medium ordinarily used in the culture of the mammalian cells except that it contains the metaphase-synchronizing agent. Examples of the culture medium include minimum essential medium (MEM), Dulbecco's modified eagle medium (D-MEM) and 10% fetal bovine serum (FBS)-containing minimum essential medium (S-MEM), but the culture medium is not limited to those mentioned above. These culture media for culturing mammalian cells are commercially available, and commercially available products may preferably be used.

The culturing time in the step (1) is not restricted and may preferably be about 15 minutes to 1 hour, more preferably about 20 to 40 minutes. The culturing temperature may preferably be the body temperature of the mammal or in the vicinity thereof (preferably ±3° C.). In the present invention, unless otherwise specified, in any culturing steps, the culturing temperature may preferably be the body temperature of the mammal or in the vicinity thereof.

The step (1) may preferably be carried out by replacing the culture medium of the mammalian cells preliminarily cultured on a support with a culture medium containing the metaphase-synchronizing agent. In this case, the population of cells before replacing the culture medium to that containing the metaphase-synchronizing agent may preferably include cells in the logarithmic growth phase. In cases where the step (1) is carried out by replacing the culture medium, the above-described explanation of step (1) is that for the culture after replacing the culture medium. The culture before replacing the culture medium may be carried out by a conventional method.

In the subsequent step (2), by shaking the support on which the cells are attached during the culturing in step (1), a portion of the cells is made to detach from the support. Since M phase cells are substantially spherical and the adhesion with the support is weak, they are likely to be detached from the support by the shaking treatment. Therefore, the percentage of M phase cells in the population of the cells detached from the support is considerably higher than that in the population of the cells on the support. The term "shaking treatment" herein means a treatment for exerting acceleration to the cells on the support in the direction parallel to the support (i.e., the horizontal direction when the support is held horizontally) by moving the support, and includes reciprocal linear movement, circular movement and other arbitrary movements. The conditions of shaking treatment are not limited as long as M phase cells are detached. The shaking treatment may preferably be carried out under an acceleration in the direction parallel to the support of about 0.001 to 30 g ("g" herein means gravity acceleration), more preferably about 0.2 to 30 g, still more preferably about 3 to 30 g, still more preferably about 10 g to 20 g, and the treatment time may preferably be about 10 seconds to 2 minutes, more preferably about 30 seconds to 1 minute and 30 seconds. The shaking treatment may be carried out by, for example, linearly or curvedly shaking the support with a shaking width (in case of linear reciprocating movement, the distance from an end to the other end of the movement; and in case of circular movement, the diameter of the circle) of 1 to 10 mm at a revolution of 1000 to 5000 rpm (in case of linear reciprocating movement, 1000 to 5000 reciprocals), preferably with a shaking width of 2 to 4 mm at a revolution of 2500 to 3500 rpm, such that the acceleration is within the preferred scope mentioned above. The shaking treatment may be carried out by shaking the support with a bare hand (especially in cases where the acceleration is not more than 0.1 g). In cases where the shaking treatment is carried out under an acceleration of not less than 0.2 g, which is more preferred as mentioned above, so as to increase the number of M phase cells collected, the shaking treatment may be carried out by mounting the support (petri dish or the like) on a shaking machine such as a commercially available mixer. Even if the support is shaken with a bare hand under an acceleration of less than 0.2 g, the cells are not only subjected to the acceleration in the direction parallel to the support, but also subjected to water pressure by the culture medium due to the movement of the culture medium. Therefore, by appropriately adjusting the size of the support (diameter in cases where the support is a petri dish) and the amount of the culture medium, M phase cells may be comparatively effectively collected even with a small acceleration. The size of the support and the amount of the culture medium may appropriately be selected by routine experiments. For example, in the case where the support is a petri dish having a diameter of 10 cm, the amount of the culture medium may preferably be about 4 to 6 ml. It should be noted, however, that the number of the collected M phase cells is larger by giving a larger acceleration by using a shaking machine such as a mixer. The cells detached from the support may easily be collected by, for example, centrifuging the supernatant.

In the subsequent step (3), cells having a diameter of not less than 20 μm, preferably not less than 20 μm and not more than 30 μm, are collected from the population of cells collected in step (2). The cells to be collected in step (3) may preferably be those which have clear boundary of the cell membrane, and which are substantially spherical. In cases where the cell is not spherical, the term "diameter" herein means the shorter diameter. The collection of the cells may be carried out by sucking the cell one by one with a pipette under a microscope. The pipette may preferably have an inner diameter of about 20 μm, and the cells having the above-mentioned preferred diameter may be collected by collecting the cells passing through the pipette while being slightly deformed. This operation may preferably be carried out by placing the cells collected in step (2) in a culture medium containing the metaphase-synchronizing agent, and collecting the cells while keeping the cells to be placed in this culture medium. The operation may preferably be carried out within 1 hour, more preferably within 45 minutes. The temperature of the culture medium during the collection operation may be 10 to 25° C., preferably 15 to 20° C.

The percentage of the normal M phase cells in the population of cells collected by the method of the present invention may be further increased by carrying out additional steps of shaking the support; discarding the cells detached from the support together with the culture medium; and culturing the cells remaining on the support in the presence of the metaphase-synchronizing agent, between steps (1) and (2). These additional steps may be conducted at least once, and the cycle of the additional steps may be repeated. The additional steps may preferably be carried out totally once to thrice. The preferred conditions of the shaking treatment carried out in the additional steps may be the same as the above-mentioned preferred conditions of the shaking treatment in step (2), and the preferred conditions of the culturing on the support in the presence of the metaphase-synchronizing agent are the same as the above-mentioned preferred conditions of the culturing in step (1). The reason why the percentage of the M phase cells is further increased by carrying out the additional steps is presumed as follows. By carrying out the additional steps at least once, most of the cells which were in M phase at the completion of the culturing in step (1) are discarded together with the culture supernatant, and the cells remaining on the support are in $G_1$ to $G_2$ phase. Since the cells in $G_1$ phase after metaphase do not substantially exist in the remaining cells, the percentage of the M phase cells at the time of collection after the culturing is further increased.

By the method described above, the percentage of the M phase cells in the population of collected cells may be made extremely high. In the Examples described below, the percentage of the M phase cells in the population of the collected cells was as high as 99.1%.

The method for collecting $G_1$ phase cells according to the present invention will now be described. As for the type of the mammalian cells subjected to this method, and as for steps (1) and (2), the above descriptions for the method for collecting M phase cells may exactly be applied. Therefore, the operations up to step (2) may be carried out in the same manner as described above. In this method too, it is preferred to carry out additionally, at least once, preferably once to thrice, steps of shaking the support; discarding the cells detached from the support together with the culture medium; and culturing the cells remaining on the support in the presence of the metaphase-synchronizing agent.

In step (3) of the method for collecting $G_1$ phase cells according to the present invention, the cells collected in step (2) are cultured in the absence of the metaphase-synchronizing agent. This culturing may be carried out in accordance with the conventional method for culturing the mammalian cells. Thus, the culturing may be carried out in a well-known culture medium mentioned above for culturing the mammalian cells at a temperature same as the body temperature of the mammal or a temperature in the vicinity thereof. The culturing time may preferably be about 15 minutes to 1 hour, more preferably about 20 to 40 minutes. By this culturing, the M phase cells collected in step (2) proceed to $G_1$ phase.

In the subsequent step (4), cells having a diameter of not more than 15 μm, preferably not less than 12 μm and less than 15 μm, are collected from the population of the cultured cells. The cells to be collected in step (4) may preferably be those which have clear boundary of the cell membrane, and which are substantially spherical. In cases where the cell is not spherical, the term "diameter" herein means the shorter diameter. The collection of the cells may be carried out by sucking the cell one by one with a pipette under a microscope. The pipette may preferably have an inner diameter of about 15 μm, and the cells having the above-mentioned preferred diameter may be collected by collecting the cells passing through the pipette smoothly without being deformed. This operation may be carried out while observing the culture after step (3) under a microscope. The operation may preferably be carried out within 1 hour, more preferably within 45 minutes. The temperature of the culture medium during the collection operation may be 10 to 25° C., preferably 15 to 20° C.

By the method described above, the percentage of the $G_1$ phase cells in the population of cells may be made extremely high. In the Examples described below, the percentage of the $G_1$ phase cells in the population of the collected cells was as high as 97.9%.

A population of cells in $G_1$ phase may also be obtained by culturing the cells in M phase collected by the above-described method according the present invention so as to allow each of the cells to divide into two cells; and recovering uniformly divided cells separately. In this case, the culturing may be carried out by using an ordinary culture medium not containing a metaphase-synchronizing agent according to a conventional method. The culturing time may preferably be about 15 minutes to 1 hour, more preferably about 20 to 40 minutes.

In the population of M phase cells or $G_1$ phase cells collected by the method according to the present invention, the cell cycles of the cells in the population are substantially synchronized. Therefore, they are very suited for the studies what biochemical reactions occur during a specific cell cycle, and for the studies of the mechanism of the cell proliferation.

It was first discovered that by carrying out nuclear transplantation using the cells collected by the method of the present invention as nuclear donors, the probability that the reconstructed embryos that grow at least to compacted morula is significantly increased. Thus, the present invention also provides a method for nuclear transplantation comprising transplanting said cell collected by said method according to the present invention, or at least the nucleus thereof, to an enucleated oocyte; and culturing the resulting cell to allow it to divide. This nuclear transplantation method may be carried out by a conventional method except that the cells collected by the above-described method according to the present invention are used as the nuclear donors, and a preferred example is described in detail in the Examples below. The nuclear transplantation may be carried out not only by transplanting the whole cell used as the donor cell as described in Examples below, but also may be carried out by transplanting at least the nucleus of the cells. In the latter case, the nucleus may be transplanted together with the cytoplasm.

By making a mammal conceive the divided cells grown at least to compacted morula, to make the mammal impregnated, a somatic cell clone may be obtained. In this case, the mammal to be impregnated belongs to the same species as the mammal from which the embryo was originated. Impregnation of the mammal may be carried out by a conventional method well-known in the art.

EXAMPLES

The present invention will now be described in more detail by way of examples thereof. Before describing each Example, the method for preparation of the cells, the method for synchronizing the cells to metaphase, the method for preparing preparations for investigating the cell cycle and for observing the preparation, the method for statistic analysis and the like will be described.

(1) Fetal Fibroblast Cells

As the bovine fibroblast cells (Japanese black), the cells from a fetal at Day 54 from conception were used. The recovered fetus was aseptically minced and digested with trypsin. The cell suspension was recovered and cultured in Dulbecco's modified eagle medium (D-MEM, Gibco BRL, Cat No. 11885-084, MD, USA), followed by storing frozen cells (one passage). For experiments, the frozen stored cells seeded on a 10 cm plastic petri dish (Falcon, 353003) were once subcultured, and the cells grown to logarithmic growth phase were used.

(2) Synchronization to Metaphase

For synchronization to metaphase, 10% FBS-containing minimum essential medium (S-MEM, Cat. No.11385-036, Gibco BRL, MD, USA) supplemented with 2-methoxyestadiol (2-MeOE$_2$, Cat No.M6383, Sigma chemical Co., MO, USA) to a concentration of 0.5 μM or 1 μM was used.

(3) Preparation of Preparations of Fetal Fibroblast Cells and Observation Thereof Fetal fibroblast cells were recovered by collecting the medium containing the cells in a 15 ml test tube and by centrifuging the medium (180 g, 5 minutes). After the centrifugation, the cell precipitate was resuspended with a small amount of the medium, and the resulting cell suspension was uniformly smeared on a slide glass. The slide glass was air-dried at room temperature and the cells were fixed (99.9% ethanol, 5 minutes) to prepare preparations.

Each preparation was stained with Hoechst 33342 (Sigma Chemical Co, MO, USA) and observed with a fluorescence microscope. Only the cells having clear boundary of cell membrane were used for judgment. In Comparative Examples 1 and 2, the cells in prophase, metaphase, anaphase and telophase of cell cycle were classified into the cells in mitotic phase (M phase). The cells containing only one nucleus covered with a nuclear membrane were judged as the cells in interphase. The cells in which the nucleus in the cytoplasm is fragmented, the cells containing no nucleus in the cytoplasm, and the cells having a lot of nuclei in the cytoplasm were judged as abnormal cells. In Examples 1 and 2, M phase cells were further classified into normal metaphase cells (the one nucleus in metaphase is located in the cytoplasm) and abnormal metaphase cells (the two or more nuclei in metaphase are located in the cytoplasm). The cells in interphase were classified into normal interphase cells (only one nucleus having nuclear membrane exists in the cytoplasm) and abnormal interphase cells (two or more nuclei having nuclear membrane exist in the cytoplasm, or the nucleus in the cytoplasm is fragmented).

(4) Statistic Analysis

The values obtained in Comparative Examples 1 and 2, and in Example 4 were analyzed by ANOVA, and values having a level of significance of not more than 5% was judged as significant.

(5) Cell Culture

Unless otherwise specified, cells were cultured at 35 to 40° C. The selection of the cells using a pipette was carried out at 10 to 25° C.

Comparative Example 1

Shaking Treatment

The D-MEM medium in a plastic petri dish (diameter: 10 cm) containing cells in logarithmic growth phase was replaced with 5 ml of S-MEM (not containing 2-MeOE$_2$), and culturing of the cells was continued. Thirty minutes later, the whole culture supernatant was recovered after subjecting the petri dish to shaking treatment, or without the shaking treatment. The shaking treatment was carried out by intimately attaching the bottom plate of the plastic petri dish to a mixer (IKEDA RIKA, D-10) and driving the mixer to circularly move the petri dish for 1 minute (3000 rpm, diameter of circular movement: 0.3 cm). The number of cells was counted using an aliquot of the recovered culture supernatant, and the remaining culture supernatant was centrifuged (1000 rpm, 5 minutes). The cell pellet was resuspended in a small amount of the medium and the obtained cell suspension was smeared on a slide glass.

The influence by the shaking treatment on the number of the cells adhered to the bottom surface of the plastic petri dish and on the cell cycle of the cells was investigated. The plastic petri dish after discarding the culture supernatant was washed with phosphate buffered saline(−) (hereinafter referred to as "PBS(−)") and 0.25% trypsin solution was added, thereby peeling off the cells attached to the bottom surface of the petri dish. After the peeling off, the number of cells was counted using an aliquot of the cell suspension. The remaining suspension was centrifuged and the precipitate was smeared in the same manner as described above for the culture supernatant. The smear preparation was air-dried, fixed, stained and observed.

As a result, in the case where the cells were recovered from the culture supernatant without the shaking treatment, $0.03 \times 10^6$ cells were recovered. Among the cells, 13.7% were in M phase, 66.5% were in interphase, and 19.8% were abnormal cells. On the other hand, in the case where the cells were recovered from the culture supernatant after carrying out the shaking treatment, $0.19 \times 10^6$ cells, that is, about 6 times that recovered without the shaking treatment, were recovered. Among the recovered cells, 26.1% were in M phase, 66.7% were in interphase, and 7.3% were abnormal cells. Thus, by conducting the shaking treatment, the percentage of the M phase cells in the culture supernatant was significantly ($P<0.05$) increased. Although the percentage of the normal interphase cells was not changed by the shaking treatment, abnormal cells were significantly ($P<0.05$) decreased (Table 1).

As for the cells adhered to the bottom surface of the petri dish, which were recovered by the aid of digestion with trypsin, $4.87 \times 10^6$ cells were recovered and 98.1% thereof were interphase cells in the case where the shaking treatment was not performed. On the other hand, in the case where the shaking treatment was performed, $3.60 \times 10^6$ cells were recovered, and 98.5% thereof were interphase cells. Influence by the shaking treatment on the number of the cells adhered to the bottom of the plastic petri dish and on the percentage of the cells in the respective cell cycle was not observed ($P>0.05$) (Table 2).

TABLE 1

Number of Cells Recovered by Shaking Treatment from Culture Supernatant and Their Cell Cycles (Comparative Example 1)

| Shaking Treatment | Number of Replicates | Number of Recovered Cells (mean ± SD) | Number of Observed Cells | Number of Metaphase Cells (mean ± SD(%)) | Number of Normal Interphase Cells (mean ± SD(%)) | Number of Abnormal Cells (mean ± SD(%)) |
|---|---|---|---|---|---|---|
| − | 4 | $0.03 ± 0.01 \times 10^6$ | 4311 | 587 (13.7 ± 1.6[a]) | 2864 (66.5 ± 3.5) | 860 (19.8 ± 2.1[a]) |
| + | 5 | $0.19 ± 0.15 \times 10^6$ | 4066 | 1084 (26.1 ± 3.8[b]) | 2663 (66.7 ± 3.7) | 319 (7.3 ± 2.8[b]) |

[a,b]There were significant difference between the cases with and without the shaking treatment ($P < 0.05$)
SD: standard deviation

TABLE 2

Number of Cells Recovered by Shaking Treatment from Bottom Surface of Plastic Petri Dish and Their Cell Cycles (Comparative Example 1)

| Shaking Treatment | Number of Replicates | Number of Recovered Cells (mean ± SD) | Number of Observed Cells | Number of Metaphase Cells (mean ± SD(%)) | Number of Normal Interphase Cells (mean ± SD(%)) | Number of Abnormal Cells (mean ± SD(%)) |
|---|---|---|---|---|---|---|
| − | 4 | $4.87 ± 1.39 \times 10^6$ | 4044 | 40 (1.0 ± 0.2) | 3966 (98.1 ± 0.2) | 38 (0.9 ± 0.3) |
| + | 5 | $3.60 ± 1.37 \times 10^6$ | 4010 | 28 (0.8 ± 0.5) | 3949 (98.5 ± 0.6) | 33 (0.7 ± 0.3) |

Comparative Example 2

Combination of Metaphase-synchronizing Agent and Shaking Treatment

How the cell cycles of the cells recovered from the culture supernatant change by combination of the metaphase-synchronizing agent (2-MeOE$_2$) and the shaking treatment was investigated with successively repeating the step of shaking treatment and the subsequent recovery 3 times. That is, D-MEM medium in a petri dish containing cells in logarithmic growth phase was replaced with 5 ml of S-MEM medium (containing 0.5 μM or 1.0 μM 2-MeOE$_2$), and the culturing was continued. Thirty minutes later, the shaking treatment was carried out as in Comparative Example 1 and the culture supernatant was centrifuged (1000 rpm, 5 minutes) to recover the cells (first time recovered cells). To the plastic petri dish after discarding the culture supernatant, 5 ml of fresh S-MEM medium (containing 0.5 μM or 1.0 μM 2-MeOE$_2$) was added and the culturing was continued for another 30 minutes. Thirty minutes later, shaking treatment was performed as in the first time, and the culture supernatant was centrifuged to recover the cells (second time recovered cells). To the plastic petri dish after discarding the culture supernatant, 5 ml of fresh S-MEM medium (containing 0.5 μM or 1.0 μM 2-MeOE$_2$) was added and the culturing was continued for another 30 minutes. Thirty minutes later, shaking treatment was performed as in the first time and the second time, and the culture supernatant was centrifuged to recover the cells (third time recovered cells). The cells obtained using different concentrations of the metaphase-synchronizing agent and obtained in different times of recovery were respectively resuspended in a small amount of the medium and smear preparations were prepared. The smear preparations were air-dried, fixed, stained and observed.

By combination of the synchronization of the cell cycle by 2-MeOE$_2$ and the shaking treatment, the percentage of the M phase cells was increased (28.8 to 81.2%) when compared to the case where only the shaking treatment was performed without the treatment with 2-MeOE$_2$ (Comparative Example 1, 26.1%) (Table 3). As for the percentage of the M phase cells among the first time, second time and third time recovered cells, respectively, the percentage was significantly higher (P<0.05) when the concentration of 2-MeOE$_2$ was 1.0 µM than when the concentration of 2-MeOE$_2$ was 0.5 µM. In cases where the cells were treated with 0.5 µM 2-MeOE$_2$ for 30 minutes, the percentage of M phase cells was significantly higher (P<0.05) in the second time and third time recovered cells than in the first time recovered cells (Table 3). On the other hand, in cases where the cells were treated with 1.0 µM of 2-MeOE$_2$ for 30 minutes, the percentage of the M phase cells was significantly increased (P<0.05) with the number of times of recovery of the cells. On the other hand, the percentages of the normal interphase cells and abnormal cells were significantly lower in the second time and third time recovered cells than in the first time recovered cells irrespective whether the concentration of the 2-MeOE$_2$ was 0.5 µM or 1.0 µM.

Example 1

Collection of M Phase Cells

D-MEM medium in a petri dish containing cells in logarithmic growth phase was replaced with 5 ml of S-MEM medium containing 1.0 µM 2-MeOE$_2$, and the culturing was continued. Thirty minutes later, the shaking treatment was carried out as in Comparative Example 1 and the culture supernatant was discarded. To the petri dish after discarding the culture supernatant, fresh S-MEM medium containing 1 µM 2-MeOE$_2$ was added and the culture was continued for another 30 minutes. Thirty minutes later, the shaking treatment was carried out as described above and the culture supernatant was centrifuged (1000 rpm, 5 minutes) to recover the cells (second time recovered cells). An aliquot of the collected cells was transferred to D-MEM medium containing 1 µM 2-MeOE$_2$, and substantially spherical cells having clear boundary of cell membrane and having a diameter slightly larger than 20 µm were selected within 30 minutes using a glass pipette (COOK, Cat.No.PBBP-2000) having an inner diameter of 20 µm. The selected cells were immediately transferred to phosphate buffered saline (D-PBS) containing Hoechst33342 and 1 µM 2-MeOE$_2$, and cell cycles were determined under an inverted fluorescence microscope.

Thus, the cells were synchronized to M phase by 1 µM 2-MeOE$_2$ and the cells in the culture supernatant of the second culture were recovered after the shaking treatment. The cells having a diameter of not less than about 20 µm were selected therefrom and observed. As a result, 99.1% of the collected cells were M phase cells (Table 4). Further, most (98.8%, 243/246) of the collected cells were normal metaphase cells.

TABLE 3

Influence by 2-MeOE$_2$ Concentration and Number of Times of Recovery on Cell Cycles of Cells Recovered by Combination of Cell Cycle Synchronization and Shaking Treatment (Comparative Example 2)

| 2-MeOE$_2$ Concentration | Times of Recovery | Number of Replicates | Number of Observed Cells | Number of Metaphase Cells (mean ± SD(%)) | Number of Normal Interphase Cells (mean ± SD(%)) | Number of Abnormal Cells (mean ± SD(%)) |
|---|---|---|---|---|---|---|
| 0.5 µM | First Time | 4 | 2046 | 591 (28.8 ± 3.0$^a$) | 1142 (55.8 ± 3.6$^a$) | 313 (15.4 ± 5.8$^a$) |
|  | Second Time | 4 | 2078 | 940 (45.2 ± 7.9$^{bc}$) | 1003 (48.3 ± 49$^{bc}$) | 135 (6.6 ± 4.2$^{bc}$) |
|  | Third Time | 4 | 2052 | 945 (46.0 ± 7.5$^c$) | 977 (47.6 ± 4.7$^c$) | 130 (6.4 ± 3.9$^c$) |
| 1 µM | First Time | 4 | 2033 | 1017 (50.1 ± 8.6$^d$) | 784 (38.5 ± 6.8$^d$) | 232 (11.4 ± 5.6$^d$) |
|  | Second Time | 4 | 2075 | 1614 (77.7 ± 5.4$^e$) | 398 (19.2 ± 5.0$^{ef}$) | 63 (3.1 ± 1.5$^{ef}$) |
|  | Third Time | 4 | 2126 | 1728 (81.2 ± 5.0$^f$) | 330 (15.6 ± 3.3$^f$) | 68 (3.2 ± 1.7$^f$) |

$^{a-f}$There were significant differences between different symbols depending on the concentration and the number of times of recovery (P < 0.05)

TABLE 4

Selection by Size of Cells Recovered by Cell Cycle-Synchronization and Shaking Treatment (Example 1)

| Inner Diameter of Pipette | Number of Replicates | Number of observed cells | Number of Normal Metaphase Cells (mean ± SD(%)) | Number of Abnormal Metaphase Cells (mean ± SD(%)) | Number of Normal Interphase Cells (mean ± SD(%)) | Number of Abnormal Interphase Cells (mean ± SD(%)) |
|---|---|---|---|---|---|---|
| 20 µm | 4 | 249 | 243 (97.8% ± 2.1) | 3 (1.3 ± 2.5) | 3 (1.0 ± 1.1) | 0 (0.0 ± 0.0) |

Example 2

Collection of G₁ Phase Cells (1)

The second time recovered cells obtained in Example 1 were transferred to 10% FBS-containing D-MEM medium (not containing 2-MeOE$_2$), and cultured for 30 minutes in a CO$_2$ incubator. Thirty minutes later, substantially spherical cells having clear boundary of cell membrane and having a diameter slightly smaller than 15 μm were selected within 30 to 45 minutes using a glass pipette (COOK, Cat. No. PBBP-1500) having an inner diameter of 15 μm. The selected cells were immediately stained with Hoechst33342 and cell cycles were determined under an inverted fluorescence microscope.

Thus, by recovering cells in the culture supernatant of the second culture in a medium not containing 2-MeOE$_2$ for 30 minutes, and by subsequently selecting the cells with a diameter of not more than about 15 μm, the percentage of interphase cells was 97.9%, and 95.5% (148/155) thereof were normal interphase cells (Table 5).

TABLE 5

Selection by Size of Cells Recovered after Culturing (30 minutes) by Cell Cycle-Synchronization and Shaking Treatment (Example 1)

| Inner Diameter of Pipette | Number of Replicates | Number of observed cells | Number of Normal Metaphase Cells (mean ± SD(%)) | Number of Abnormal Metaphase Cells (mean ± SD(%)) | Number of Normal G1 phase Cells (mean ± SD(%)) | Number of Abnormal G1 Phase Cells (mean ± SD(%)) |
|---|---|---|---|---|---|---|
| 15 μm | 3 | 156 | 1 (2.1% ± 3.6) | 0 (0.0 ± 0.0) | 148 (94.8 ± 1.0) | 7 (3.1 ± 2.7) |

Example 3

Collection of G₁ Phase Cells (2)

D-MEM medium in a petri dish containing cells in logarithmic growth phase was replaced with 5 ml of S-MEM medium containing 1 μM 2-MeOE$_2$, and the culturing was continued. Thirty minutes later, the shaking treatment was carried out as in Comparative Example 1 and the culture supernatant was discarded. To the petri dish after discarding the culture supernatant, fresh S-MEM medium containing 1 μM 2-MeOE$_2$ was added and the culture was continued for another 30 minutes. Thirty minutes later, the shaking treatment was carried out as described above and the culture supernatant was centrifuged (1000 rpm, 5 minutes) to recover the cells (second time recovered cells). The recovered cells were plated to TCM199 medium (Gibco BRL, Cat No. 12340-030, MD, USA, containing 1 μM 2-MeOE$_2$) containing 5% fetal bovine serum (FBS), and substantially spherical cells having clear boundary of cell membrane and having a diameter slightly larger than 20 μm were selected within 60 minutes using a glass pipette (COOK, Cat. No. PBBP-2000) having an inner diameter of 20 μm (M phase cells). The selected cells were cultured in a CO$_2$ incubator (5%CO$_2$ and 95% air) at 38° C., and incubated therein for 30 minutes under an atmosphere. Within 30 minutes after the incubation, the cells uniformly divided into two cells were selected and the cells were recovered after separating the two cells into a single cell (G$_1$ phase cells).

Example 4, Comparative Example 3

Using the cells of which cell cycles were not synchronized (Comparative Example 3), or the cells synchronized to G$_1$ phase recovered in Example 3 (Example 4) as nuclear donors, nuclear transplantation was carried out, and the fusion of membranes between the nuclear donor and the cytoplasm of the enucleated matured oocyte, cleavage to two-cell stage embryo or eight-cell stage embryo, and development to compacted morula or more were compared. The cells of which cell cycles were not synchronized were recovered by culturing fetal fibroblast cells until the cells occupied about 80% of area of the bottom surface of wells of a 96-well plate (Nunc, 167008) (80% confluent cells) and treating the cells with trypsin.

Enucleated oocytes were prepared by maturating bovine ovarian follicle eggs in vitro (19 to 20 hours, 5% CO$_2$, 95% air); removing cumulus cells in 0.1% hyaluronidase-supplemented PBS(−); selecting oocytes which had primary polar body and uniform cytoplasm; and removing the nucleus of the oocytes using a micromanipulator[13]. Confirmation of removal of nucleus was carried out by incubating the removed cytoplasm of the egg in a medium containing Hoechst 33342 for 20 to 30 minutes at 39° C., and observing the resultant under an inverted fluorescence microscope. The enucleated oocytes of which cytoplasm removed therefrom contained a nucleus were used for the experiments. In nuclear transplantation, nuclear donor (whole cell) was inserted into the perivitelline space of the enucleated oocyte, and direct current voltage was applied (30V/150 μm, 10 micro seconds, once) in 0.3 M mannitol solution[14] containing 0.05 mM CaCl$_2$ and 0.1 mM MgSO$_4$ at 23 to 25 hours after in vitro maturation. Thereafter, complex activation treatment[15] using Ca ionophore and cycloheximide (Sigma Chemical Co., MO, USA) and developmental culturing by the co-culture with bovine oviduct epithelium were carried out. An aliquot of the reconstructed embryos was stained with Hoechst 33342 for 30 minutes at 19 hours from the application of the direct current (d.c.) voltage, and the resultant was observed under an inverted fluorescence microscope. Those containing a nucleus in the cytoplasm were judged as fused embryos. The rate of fusion was calculated by dividing the number of fused embryos with the number of prepared nucleus-transplanted embryos. Using the remaining nucleus-transplanted embryos, cleavage to two-cell or eight-cell embryos was evaluated on the third day from the nuclear transplantation, and development to compacted morula was evaluated on the sixth day from the nuclear transplantation. The rate of embryos successfully cleaved to two-cell or eight-cell embryos, or successfully developed to compacted morula was calculated by dividing the number of embryos successfully cleaved to two-cell or eight-cell embryos, or successfully developed to compacted morula with the estimated number of fused embryos. The estimated number of fused embryos was calculated by multiplying the number of prepared nucleus-transplanted embryos by the rate of fusion.

As a result, the rates of fusion between the nuclear donor and the enucleated oocyte were 78.7% (using 80% confluent cells) and 63.0% (using $G_1$ phase cells), respectively. Although the rate of fusion was higher in the case where 80% confluent cells were used than in the case where the $G_1$ phase cells were used, significant difference was not observed (P>0.05) (Table 6). Whether the synchronization of cell cycle was used or not did not influence on the rate of embryos successfully cleavage to two-cell or eight-cell embryos. However, the rate of embryos successfully developed to compacted morula at Day 6 was significantly higher (P<0.05) in the case where the synchronization of cell cycle was used than in the case where the synchronization of cell cycle was not used.

TABLE 6

Fusion and Development of Nucleus-Transplanted Embryos Derived from Cells Whose Cell Cycles Were Synchronized

| | | Fusion of Nucleus-Transplanted Embryos | | Development of Nucleus-Transplanted Embryos | | | | |
|---|---|---|---|---|---|---|---|---|
| | | | | Number | Estimated | | | Development Rate |
| | | Number of | | of | Number of | Cleavaged Rate (Day3) | | (Day6) |
| Donor Cell | Number of Replicates | Pulsed Embryos | Number of Fused Embryos (%) | Pulsed Embryos | Fused Embryos*** | ≧2-cell Embryo (%) | ≧8-cell Embryo (%) | ≧Compacted Morula (%) |
| 80% Confluent Cells* | 4 | 61 | 48 (78.7) | 68 | 54 | 45 (83.3) | 23 (42.6) | 15 (27.8)[a] |
| $G_1$ Phase Cells** | 4 | 54 | 34 (63.0) | 63 | 40 | 32 (80.0) | 20 (50.0) | 21 (52.5)[b] |

*No Synchronization,
**2-MeOE$_2$, shaking treatment, selection by size, and then selection by size after culturing
***Number of Embryos Subjected to Pulsed Embryos × Fusion Rate
[a,b]There was significant difference between the cases with and without the synchronization (P < 0.05)

Example 7

Impregnation of Heifers with Prepared Embryos

An aliquot of the embryos successfully developed to blastocysts were transplanted to 10 heifers such that each cow received a single embryo. Whether the cows were impregnated or not was checked by using an ultrasonic diagnosis apparatus after 20 to 26 days from the transplantation (equivalent to 27 to 33 days from conception). As a result, pregnancy of all of the 10 cows was confirmed. On 54 to 55 days after transplantation (equivalent to 60 to 63 days from conception), pregnancy was checked again. As a result, pregnancy of all of the cows except for only one cow was confirmed.

REFERENCES

[1] Terashima T and Tolmach J. Growth and nucleic acid synthesis in synchronously dividing populations of HeLa cells. Exp. Cell Res. 1963; 30: 344-362.
[2] Andreu J M and Timasheff s. Tubulin bound to colchicine forms polymers different from microtubules. Proc. Natl. Acad. Sci. USA 1982; 79: 6753-6756.
[3] Farrell K W and Wilson L. Proposed mechanism for colchicin poisoning microtubules reassembled in vitro for Strongylocentrotus purpuratus sperm tail outer doublet tubulin. Biochemistry 1980; 19: 3048-3054
[4] Stubblefield E, Klevecz R and Deaven L. Synchronizen mammalian cell culture. I. Cell replication cycle and macromolecular synthesis following erief colcemid arrest of mitosis. J. Cell Physiol. 1967; 69: 345-354.
[5] Lee J C, Field D J and Lee L L Y. Effects of nocodazole on structures of calf brain tubulin. Biochemistry 1980; 19: 6209-6215.
[6] Zieve G W, Turnbull D, Mullins J M and McIntosh J R. Production of large numbers of mitotic mammalian cells by use of the reversible microtubule inhibitor nocodazole. Exp. Cell Res. 1980; 126: 397-405.
[7] Wilmut I, Schnieke A E, McWhir J, Kind A J, Campbell K H S. Viable offspring derived from fetal and adult mammalian cells. Nature 1997; 385: 810-813.
[8] Kues W A, Carnwath J W, Niemann H, Paul D. Serum deprivation induces DNA fragmentation of porcine fetal fibroblasts. Theriogenology 2000; 53: Abstr. 228.
[9] Peura T T. Serum starvation can cause excessive DNA damage in sheep fetal fibroblasts. Theriogenology 2001; 55: Abstr. 285.
[10] Edwards J L, Dorado C M, Wilson T J, Schrick Fn. Development of cloned embryos reconstructed with serum fed or starved adult granulosa cells. Theriogenology 2001; 55: Abstr.265.
[11] Attalla H, Makela T P, Adlercreutz H and Andersson L C. 2-Methoxyestradiol arrests cells in mitosis without depolymerizing tubulin. Biochem. Biophys.Res. Commun. 1996; 228: 467-473.
[12] Attalla H, Knuutila S, Makela T P, Andersson L C and Adlercreutz H. Cytogenetic chromosomal preparations using 2-methoxyestradiol. Cancer Genet. Cytogenet. 1998; 102: 139-141.
[13] Aoyagi Y, Konishi M, Wada T, Takedomi T. Unaged bovine oocytes successfully develop to blastocyst after parcenogenic activation or nuclear transfer. Thriogenology 1994; 41: Abstr. 157.
[14] Willadsen S M. Nuclear transplantation in sheep embryos. Nature 1986, 320: 63-65.
[15] Yoshito AOYAGI and Masato KONISHI, J Reprod. Dev. 1994, 40: j5-j11

We claim:

1. A method for nuclear transplantation comprising collecting donor cells in G1 phase comprising, in the order mentioned, the steps of:

(1) culturing mammalian fibroblast cells on a support in the presence of an agent for synchronizing cell cycle to metaphase;
(2) shaking said support and recovering cells detached from said support;
(3) recovering cells having a diameter of not less than 20 μm from the cells recovered in said step (2);
(4) culturing said cells recovered in step (3) so as to allow each of the cells to divide into two cells; and
(5) recovering uniformly divided cells in step (4) separately;
(6) transplanting said donor cell recovered in step (5) or nucleus thereof into an enucleated oocyte; and
(7) culturing the resulting nuclear transferred cell to allow it to divide;
said method further comprising, between said step (1) and step (2), the additional steps of shaking said support; discarding cells detached from said support together with the culture medium; and culturing cells remaining on said support in the presence of said agent for synchronizing cell cycle to metaphase, said additional steps being carried out once to thrice.

2. The method according to claim 1, wherein said step (3) is carried out by collecting the cells having said diameter in a culture medium containing said agent for synchronizing cell cycle to metaphase.

3. The method according to claim 1, wherein said step (3) is carried out by sucking said cells with a pipette having an inner diameter of 20 μm.

4. The method according to claim 1, wherein said agent for synchronizing cell cycle to metaphase is 2-methoxyestradiol.

* * * * *